(12) United States Patent
Xu et al.

(10) Patent No.: US 12,024,483 B2
(45) Date of Patent: Jul. 2, 2024

(54) SYNTHESIS METHOD OF HYDROXYBENZYLAMINE

(71) Applicant: TAIZHOU CHUANGYUAN INDUSTRIAL TECHNOLOGY CO., LTD, Zhejiang (CN)

(72) Inventors: Changping Xu, Zhejiang (CN); Yanrong Jia, Zhejiang (CN)

(73) Assignee: TAIZHOU CHUANGYUAN INDUSTRIAL TECHNOLOGY CO., LTD, Zhejiang (CN)

( * ) Notice: Subject to any disclaimer, the term of this patent is extended or adjusted under 35 U.S.C. 154(b) by 308 days.

(21) Appl. No.: 17/639,591

(22) PCT Filed: Sep. 2, 2020

(86) PCT No.: PCT/CN2020/112960
§ 371 (c)(1),
(2) Date: Mar. 2, 2022

(87) PCT Pub. No.: WO2021/093426
PCT Pub. Date: May 20, 2021

(65) Prior Publication Data
US 2022/0289664 A1    Sep. 15, 2022

(30) Foreign Application Priority Data

Nov. 13, 2019   (CN) .......................... 201911106922.X

(51) Int. Cl.
C07C 213/00       (2006.01)
(52) U.S. Cl.
CPC ................................ C07C 213/00 (2013.01)
(58) Field of Classification Search
None
See application file for complete search history.

(56) References Cited

U.S. PATENT DOCUMENTS

| | | | | |
|---|---|---|---|---|
| 4,507,499 A * | 3/1985 | Rossetti | ................ | C07C 233/12 564/179 |
| 5,061,720 A * | 10/1991 | Walsh | .................. | C07D 277/14 548/200 |
| 5,252,573 A | 10/1993 | Barker et al. | | |
| 6,297,232 B1 * | 10/2001 | Bonnert | .................... | A61P 9/10 544/254 |
| 6,518,290 B1 * | 2/2003 | Sierra | ..................... | A61P 29/00 514/342 |
| 7,094,909 B2 | 8/2006 | Kucera et al. | | |
| 7,704,995 B2 * | 4/2010 | Buhr | .................... | C07D 403/04 544/405 |
| 2004/0137518 A1 * | 7/2004 | Lambert, III | ...... | C07K 14/4705 435/7.1 |
| 2007/0219374 A1 * | 9/2007 | Kiyokawa | ............. | C07C 213/02 546/192 |

FOREIGN PATENT DOCUMENTS

| | | |
|---|---|---|
| CN | 110803996 | 2/2020 |
| WO | 2100844 | 12/2002 |
| WO | 2016200840 | 12/2016 |
| WO | WO-2016200840 A1 * | 12/2016 |

OTHER PUBLICATIONS

N. G. Anderson, Practical Process & Research Development, 27-52, 81-111 (2000) (Year: 2000).*
K. Chichak et al., 70 Journal of Organic Chemistry, 7956-7962 (2005) (Year: 2005).*
D. Ewing et al., Journal of the American Chemical Society, 1901-1904 (1925) (Year: 1925).*
F. Goldschmidt et al, 66 Journal of the Society of Chemical Industry (1947) (Year: 1947).*
"International Search Report (Form PCT/ISA/210) of PCT/CN2020/112960", mailed on Nov. 4, 2020, with English translation thereof, pp. 1-6.
"Written Opinion of the International Searching Authority (Form PCT/ISA/237) of PCT/CN2020/112960", mailed on Nov. 4, 2020, pp. 1-4.
Katsuhide Kamei et al., "Synthesis, SAR studies, and evaluation of 1,4-benzoxazepine derivatives as selective 5-HT1A receptor agonists with neuroprotective effect: Discovery of Piclozotan," Bioorganic & Medicinal Chemistry, Nov. 2006, pp. 1978-1992.

* cited by examiner

*Primary Examiner* — Alexander R Pagano
(74) *Attorney, Agent, or Firm* — JCIP GLOBAL INC.

(57) ABSTRACT

The present invention relates to a synthesis method of hydroxybenzylamine, belonging to the technical field of organic synthesis. The principle of the method is a demethylation reaction of methoxybenzylamine in the presence of hydrobromic acid. The present invention has the characteristics that methoxybenzylamine and hydrobromic acid are distilled at reflux to remove redundant water to improve a reaction temperature and increase the concentration of hydrobromic acid in a reaction mixture, thereby enhancing the demethylation of hydrobromic acid on methoxybenzylamine and then shortening a reaction time and increasing a conversion rate; when generation of a methyl bromide gas is not observed, distillation is continued, excess hydrobromic acid is recycled to further improve the reaction temperature and increase the conversion rate and meanwhile reduce the consumption of raw material hydrobromic acid and decrease the processing capacity of the subsequent steps and the consumption of raw material sodium hydroxide.

13 Claims, 9 Drawing Sheets

SYNTHESIS METHOD OF HYDROXYBENZYLAMINE

CROSS-REFERENCE TO RELATED APPLICATION

This application is a 371 of international application of PCT application serial no. PCT/CN2020/112960, filed on Sep. 2, 2020, which claims the priority benefit of China application no. 201911106922.X, filed on Nov. 13, 2019. The entirety of each of the above mentioned patent applications is hereby incorporated by reference herein and made a part of this specification.

TECHNICAL FIELD

The disclosure relates to the technical field of organic synthesis, particularly to a synthesis method of hydroxybenzylamine.

BACKGROUND

Hydroxybenzylamine, also is named as aminomethylphenol, is an important organic intermediate and can be applied to multiple fields, for example 2-hydroxybenzylamine is recently applied to researches on silk dyeing and drugs for treating atherosclerosis and hypertension; 3-hydroxybenzylamine is applied to researches on hair dyes, antibacterial agents, antitumor drugs and the like; 4-hydroxybenzylamine is an important intermediate of digestive system drug itopride.

The existing synthesis methods of hydroxybenzylamine roughly include a hydroxybenzaldehyde method, a hydroxybenzonitrile method and a methoxybenzylamine method in terms of raw materials, the former two methods mostly have unique advantages but also have some unsatisfactory disadvantages, for example, a high pressure and expensive catalysts are needed, and the product is uneasy to separate and purify; in the methoxybenzylamine method, some people use a boron tribromide demethylation method to synthesize hydroxybenzylamine, but the yield is not high, and some people use the hydrobromic acid demethylation method for synthesis, but during the reaction, excess water is not removed by distillation and excess hydrobromic acid is not recycled, resulting in a relatively low reaction temperature and unsatisfactory reaction speed and conversion rate. In order to make up these disadvantages, commercially available hydrobromic acid with a maximum concentration of 48% is used and increase its use amount, which directly leads to the shortcomings of large raw material consumption, large processing capacity, and increased sodium hydroxide amount used for subsequent neutralization. But even so, the effect is still not ideal, and the yield is less than 90%.

SUMMARY

In the view of the problems existing in the prior art, the objective of the disclosure is to provide a synthesis method that is completed at a normal pressure without a catalyst. The synthesis method has the advantages of few consumption, short reaction time and high purity and yield of the finally obtained product.

The experimental principle of the disclosure is as follows: the methoxybenzylamine is subjected to demethylation reaction in the presence of hydrobromic acid. By taking 3-hydroxybenzylamine as an example, the reaction equation is as follows:

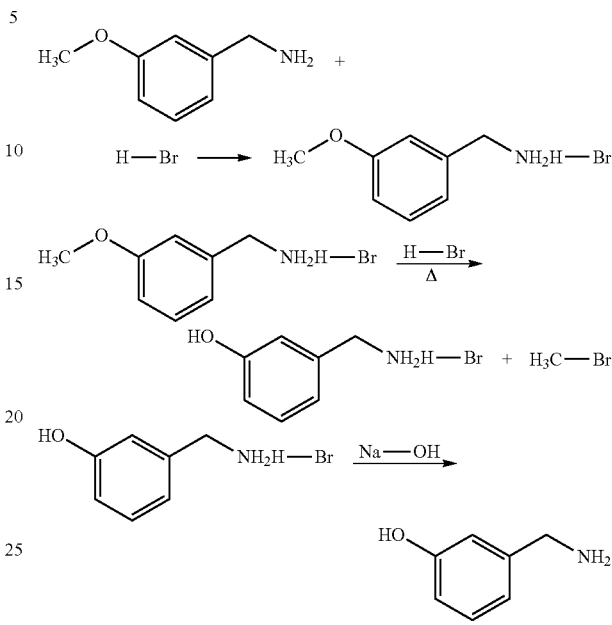

It can be seen from the above reaction formula that when hydrobromic acid is added dropwise to a reactor, a salt formation reaction firstly occurs. The reaction in this step can consume 1 equivalent of hydrobromic acid so as to remain water corresponding to the 1 equivalent of hydrobromic acid; when the demethylation reaction occurs, another 1 equivalent of hydrobromic acid is consumed so as to remain water corresponding to the another 1 equivalent of hydrobromic acid, in such a way, the concentration of hydrobromic acid in the system is reduced and meanwhile the reflux temperature when in reaction is reduced, the demethylation of hydrobromic acid is finally weakened, so as to result in prolonged reaction time and reduced product yield. Therefore, the previous chemical workers use commercially available hydrobromic acid with a maximum concentration of 48% and increase its use amount, which leads to large raw material consumption, large processing capacity, and increased sodium hydroxide amount used for subsequent neutralization but a limited effect. This invention application is proposed in response to these problems.

Provided is a synthesis method of hydroxybenzylamine, comprising the following steps:

S1: adding hydrobromic acid into a reactor equipped with a thermometer, a dropping funnel, an adjustable power heating jacket, an agitator and a distillation device, dropwise adding methoxybenzylamine under the condition of stirring until dropwise addition of methoxybenzylamine is ended, heating, and distilling to remove redundant water;

S2: when the top temperature of the distillation device reaches more than 120° C., reducing the heating rate of the adjustable power heating jacket so that the distillate flow back or is distilled out at an extremely low rate to keep the temperature in the reactor to be more than 126° C., absorbing the generated gas using an organic solvent, or freezing the generated gas for recycling until generation of no gas is observed;

S3: continuing to distill the material in step S2, recycling excess hydrobromic acid, and stopping recycling when the temperature in the reactor reaches more than 132° C.;

S4: slightly cooling the reactor in step S3, adding water into the reactor, dropwise adding a sodium hydroxide aqueous solution under the condition of cooling so that a precipitate is generated, and continuing to dropwise add the sodium hydroxide aqueous solution until the precipitate completely disappears; wherein excess water is inappropriately added so that it is not difficult to stir due to the crystallization during the subsequent cooling;

S5: extracting an organic matter insoluble into alkali in step S4 with an extraction agent, subsequently recycling the extraction agent from an organic phase, and remaining a water phase; and S6: adjusting the pH value of the water phase in step S5 by adding hydrochloric acid under the condition of ice water cooling, stirring and crystallizing, performing suction filtration, washing, and conducting vacuum drying to obtain a finished product.

Provided is the synthesis method of hydroxybenzylamine, wherein the mass concentration of hydrobromic acid in step S1 is more than 1%, preferably 10%-48%.

Provided is the synthesis method of hydroxybenzylamine, wherein methoxybenzylamine in step S1 is one of 2-methoxybenzylamine, 3-methoxybenzylamine or 4-methoxybenzylamine; wherein a target product obtained by 2-methoxybenzylamine is 2-hydroxybenzylamine, a target product obtained by 3-methoxybenzylamine is 3-hydroxybenzylamine, and a target product obtained by 4-methoxybenzylamine is 4-hydroxybenzylamine monohydrate. 4-hydroxybenzylamine that is close to an anhydrous state can be obtained by controlling the temperature and vacuum degree of the subsequent vacuum drying due to easy loss of one molecular water.

Provided is the synthesis method of hydroxybenzylamine, wherein a feeding molar ratio in step S1 of methoxybenzylamine and hydrobromic acid is 1:2-1:4, preferably 1:2.5-1:4.

Provided is the synthesis method of hydroxybenzylamine, wherein in steps S1 and S2, when excess water is removed through distillation until the top temperature of the distillation device reaches more than 120° C., the heating power is turned down so that the distillate flow back or is distilled out at an extremely low rate. The purpose of this operation is to increase the concentration of hydrobromic acid in the reaction mixture and improve the reaction temperature so that the temperature in the reactor is kept to be more than 126° C., thereby facilitating more thorough reaction and accelerating the reaction speed and then shortening the reaction time. The continuing to distill in step S3 is to further improve the reaction temperature so that the reaction further tends to be completed, and meanwhile to recycle excess hydrobromic acid, reduce the consumption of raw material hydrobromic acid and processing capacity of the subsequent steps as well as the consumption of sodium hydroxide.

Provided is the synthesis method of hydroxybenzylamine, wherein the concentration of the sodium hydroxide aqueous solution dropwise added in step S4 is 1%-60%, preferably 10%-50%.

Provided is the synthesis method of hydroxybenzylamine, wherein the extraction agent for extracting the organic matter insoluble into alkali in step S5 is an ether substance or a homologue of benzene, the ether substance is preferably ether, propyl ether, isopropyl ether, butyl ether or methyl tert-butyl ether; the homologue of benzene is preferably benzene, toluene or xylene.

Provided is the synthesis method of hydroxybenzylamine, wherein the concentration of hydrochloric acid in step S6 is 1%-37.5%, preferably 10%-37.5%.

Provided is the synthesis method of hydroxybenzylamine, wherein the pH value in step S6 is adjusted to 9-10.

Provided is the synthesis method of hydroxybenzylamine, wherein the conditions of vacuum drying in step S6 are as follows: an absolute pressure is less than 10 mmHg, rotary vacuum drying is performed for 2 h at room temperature, and then the temperature of water as a heat transfer medium is raised to 80° C. at the temperature rising rate of 10° C./h for drying until the weight of the finished product is constant.

The process flow of the disclosure is seen in FIG. 1.

The disclosure has the beneficial effects.

In the step S2, removal of excess water by heating and distilling methoxybenzylamine and hydrobromic acid at reflux is to increase the concentration of hydrobromic acid in the reaction mixture and improve the reaction temperature, thereby enhancing the demethylation of hydrobromic acid on methoxybenzylamine and then shortening the reaction time and improving the conversion rate. The disclosure has another advantage that low-concentration hydrobromic acid can be used instead of high-concentration hydrobromic acid.

The absorption or freezing recycle of the methyl bromide gas generated in step S2 facilitates environmental protection and recycle of resources.

In step S3, distillation is continued when generation of no gas is observed to further increase the reaction temperature and make the reaction more complete. At the same time, excess hydrobromic acid is recycled to reduce the consumption of raw materials and decrease the processing capacity of the subsequent steps as well as the consumption of raw material sodium hydroxide.

Therefore, the disclosure has the advantages of simple process, short reaction time, easily purified products, low raw material consumption, high reaction yield and the like.

DESCRIPTION OF THE EMBODIMENTS

The disclosure will be further explained in combination with drawings and specific embodiments, but the protective scope of the disclosure is not limited to the scope.

Figure 1:
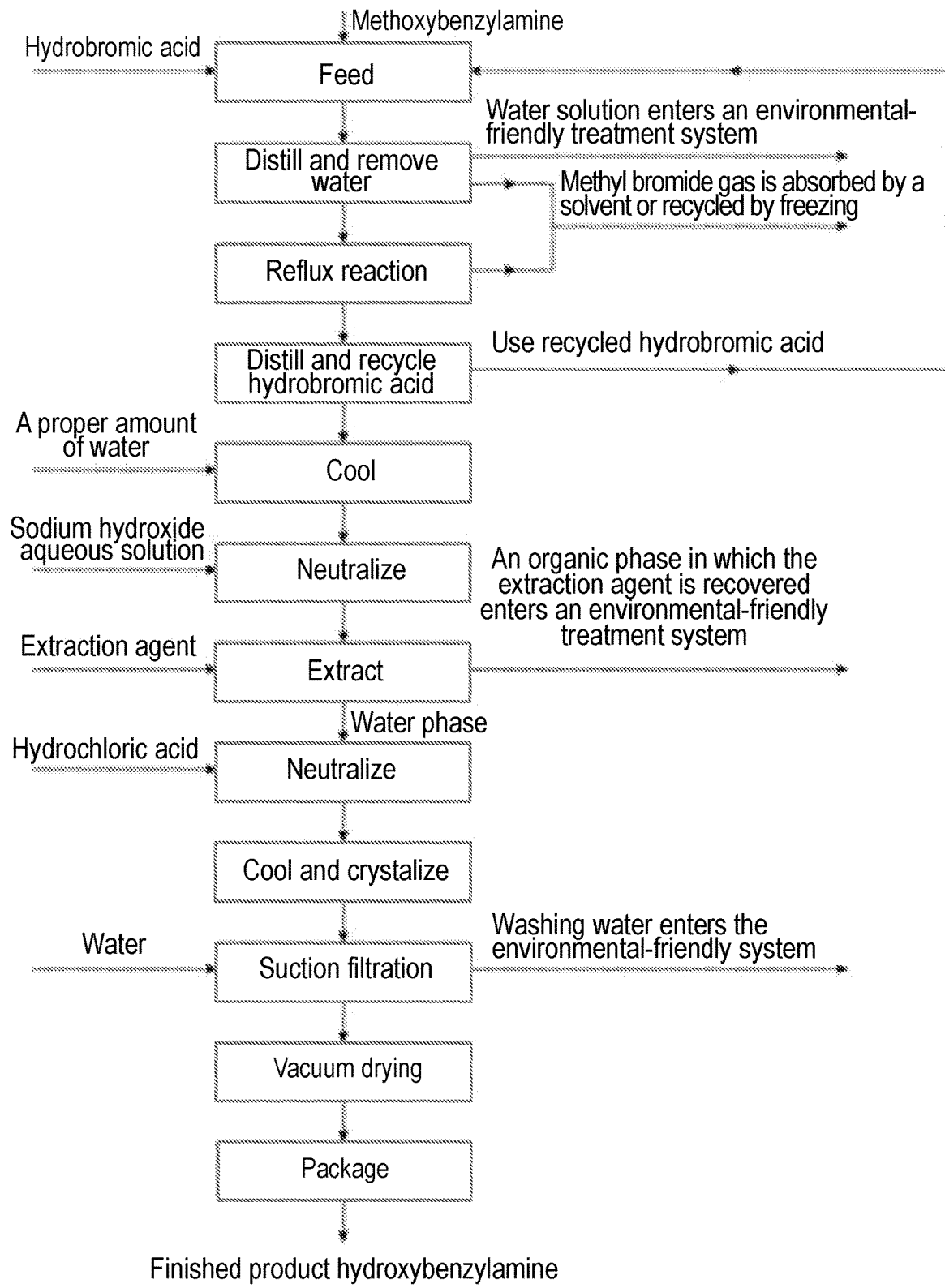
FIG. 1 is a schematic diagram of a process flow of the disclosure.
Figure 2:
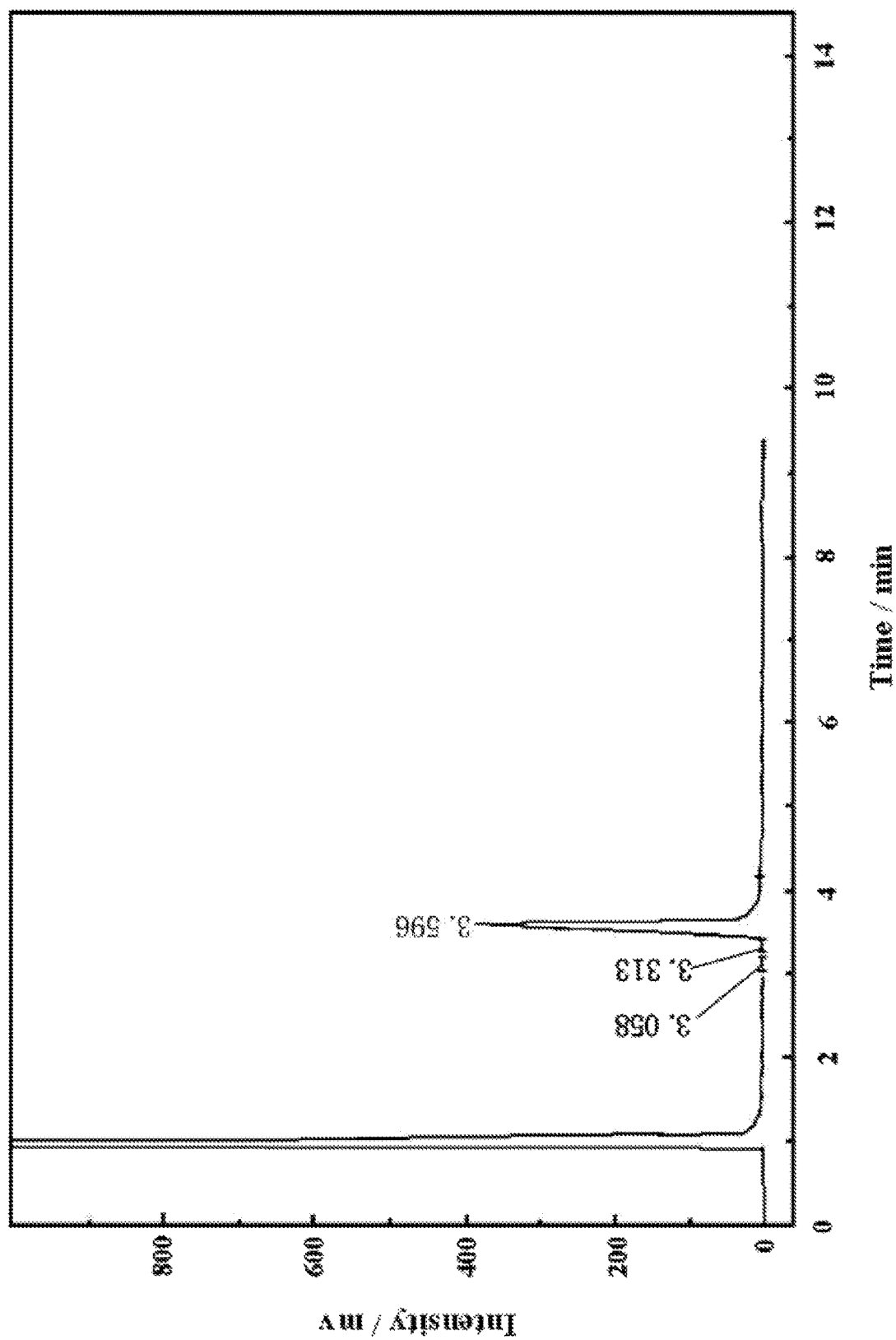
FIG. 2 is a gas chromatogram of 2-hydroxybenzylamine in Example 1.
Figure 3:
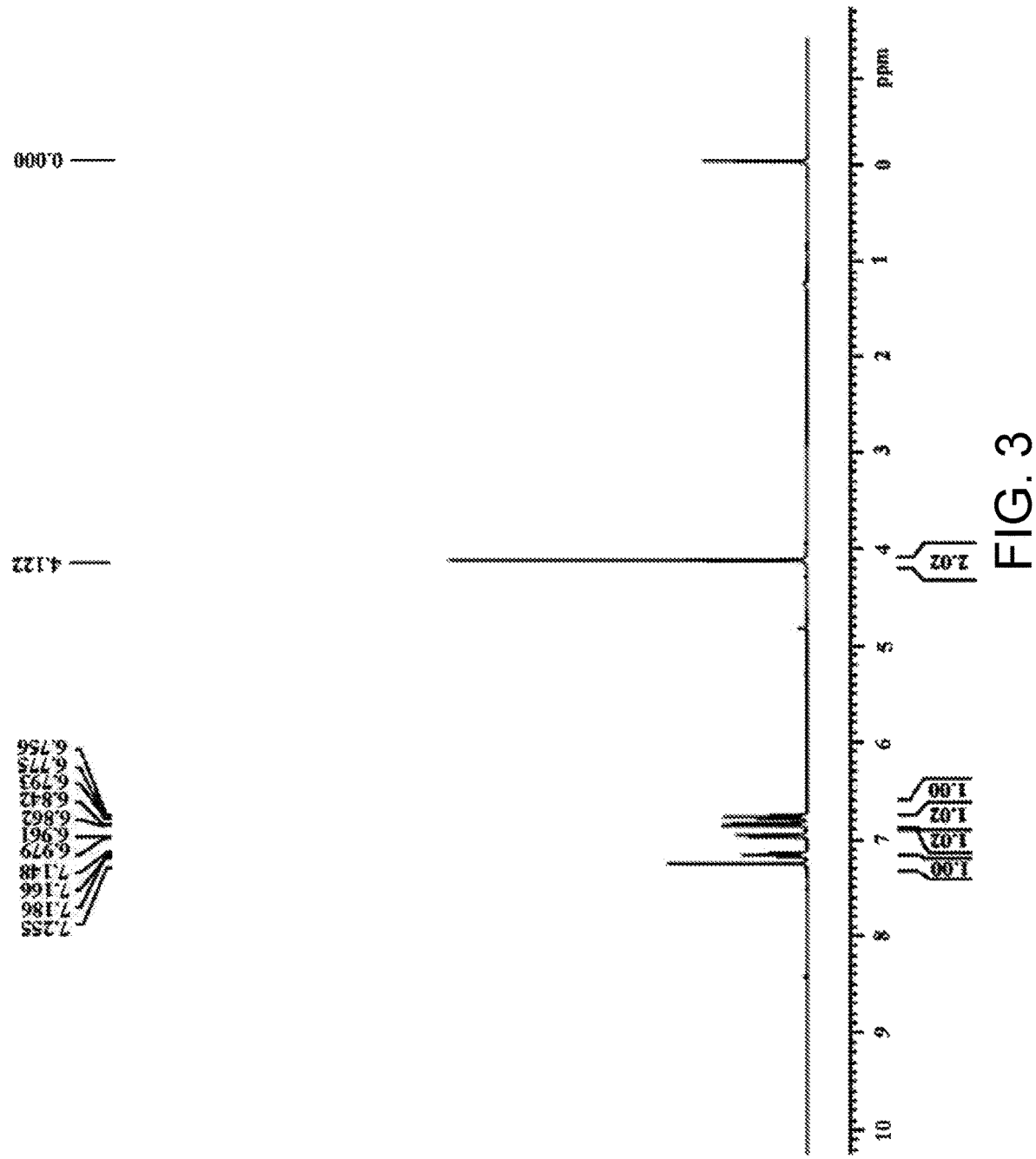
FIG. 3 is a H-NMR Spectrum of 2-hydroxybenzylamine in Example 1.

Example 1: Synthesis of 2-hydroxybenzylamine 252.8 g (1.5 mol) of 48% hydrobromic acid was added into a 0.5 L reactor equipped with a thermometer, a dropping funnel, an adjustable power heating jacket, a stirrer and a distillation device, and 68.6 g (0.5 mol) of 2-methoxybenzylamine was slowly added dropwise under the stirring of the stirrer by utilizing the dropping funnel. After the dropwise addition was completed, excess water was removed by heating and distillation until the top temperature of a distillation device reached more than 120° C. (at this moment, the temperature in the reactor reached more than 126° C.), and then the heating rate was reduced so that the distillate flowed back or was distilled out at a very slow rate, the temperature in the reactor was kept to be more than 126° C., and the generated gas was absorbed by a solvent or recycled by a refrigeration method to protect the environment until generation of no gas was observed. At this moment, the heating rate was increased again, distillation was continued, and excess hydrobromic acid was recycled until the temperature in the reactor reached more than 132° C., the reactor was slightly cooled, 80 ml of water was added, and a pre-cooled sodium hydroxide aqueous solution with a mass concentration of 33.3% was dropwise added under the condition of water cooling, so that a precipitate was generated, and then the pre-cooled sodium hydroxide aqueous solution was dropwise added again until the precipitate completely disappeared. The resulting solution was extracted and washed twice with 30 ml*2 of isopropyl ether, isopropyl ether was recovered from an organic phase, the pH value of a water phase was adjusted to 9-10 with 30% hydrochloric acid under the condition of ice water cooling, the water phase was stirred, crystallized and underwent suction filtration, and a filter cake was washed with 120 ml of water, drained and dried in vacuum, namely, a state that the absolute pressure was less than 10 mmHg was formed. The filter cake was subjected to rotary vacuum drying for 2 h at room temperature, then heated to 80° C. at the temperature rising rate of 10° C./h and dried until the weight was constant, that is, total 58.3g of finished product was obtained. By determination via Karl Fischer method, the content of water was 0.43%, and molar yield was 94.0%. It can be seen from FIG. 2 and FIG. 3 that the obtained product is indeed 2-hydroxybenzylamine, and the gas chromatography content reaches more than 99.0%. Various groups of gas chromatography data in FIG. 2 are as follows:

| Number | Retention time (min) | Peak area | Concentration (%) |
|---|---|---|---|
| 1 | 3.058 | 4393 | 0.1646 |
| 2 | 3.313 | 4084 | 0.153 |
| 3 | 3.596 | 2661392 | 99.68 |
| Total | | 2669869 | 100 |

Figure 4:
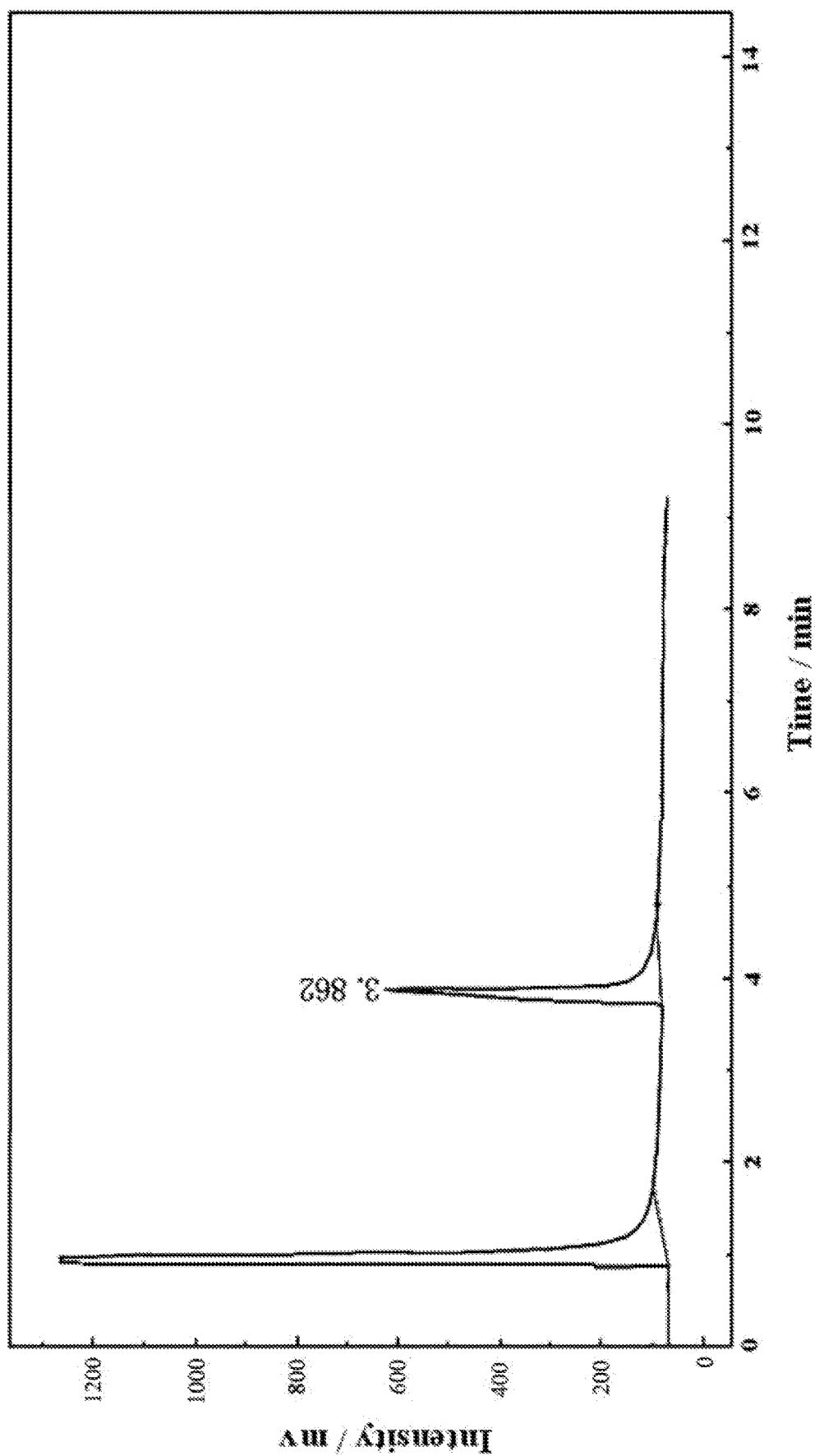
FIG. 4 is a gas chromatogram of 3-hydroxybenzylamine in Example 2.
Figure 5:
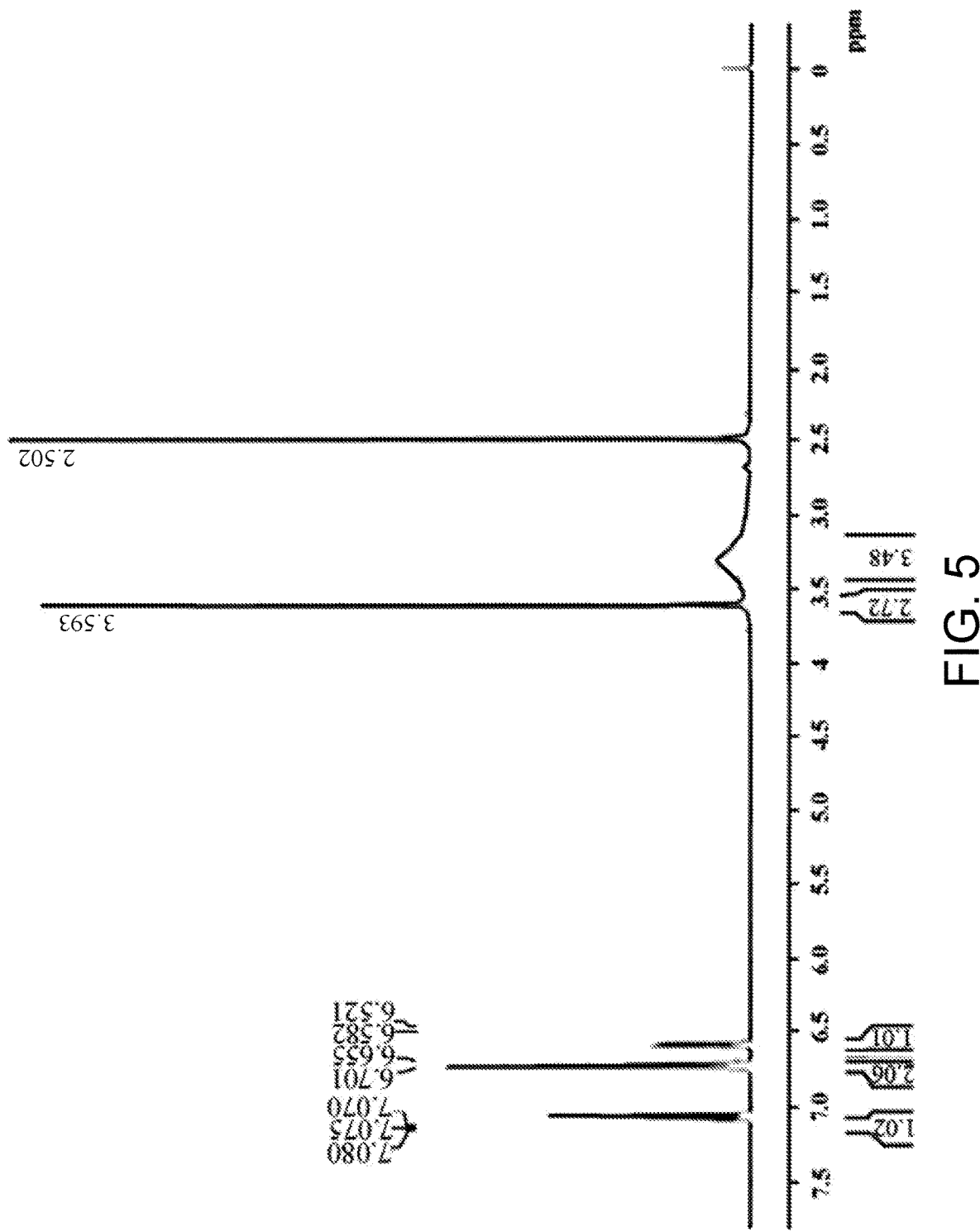
FIG. 5 is a H-NMR Spectrum of 3-hydroxybenzylamine in Example 2.

Example 2: Synthesis of 3-hydroxybenzylamine 708.0 g (3.5 mol) of 40% hydrobromic acid was added into a 1 L reactor equipped with a thermometer, a dropping funnel, an adjustable power heating jacket, a stirrer and a distillation device, and 137.2 g (1.0 mol) of 3-methoxybenzylamine was added dropwise under the stirring of the stirrer by utilizing the dropping funnel. After the dropwise addition was completed, excess water was removed by heating and distillation until the top temperature of a distillation device reached more than 120° C. (at this moment, the temperature in the reactor reached more than 126° C.), and then the heating rate was reduced so that the distillate flowed back or was distilled out at a very slow rate, the temperature in the reactor was kept to be more than 126° C., the generated gas was absorbed by a solvent or recycled by a refrigeration method to protect the environment until generation of no gas was observed. At this moment, the heating rate was increased again, distillation was continued, and excess hydrobromic acid was recovered until the temperature in the reactor reached more than 132° C., the reactor was slightly cooled, 0 ml of water was added, and a pre-cooled sodium hydroxide aqueous solution with a mass concentration of 30% was dropwise added under the condition of water cooling, so that a precipitate was generated, and then the pre-cooled sodium hydroxide aqueous solution was dropwise added again until the precipitate completely disappeared, the resulting solution was extracted and washed twice with 50 ml*2 of benzene, benzene was recovered from an organic phase, the pH value of a water phase was adjusted to 9-10 with 36.5% hydrochloric acid under the condition of ice water cooling, the water phase was stirred, crystallized and underwent suction pressure, a filter cake was washed with 250 ml of water, then drained and dried in vacuum, namely, a state that the absolute pressure was less than 10 mmHg was formed. The filter cake was subjected to rotary vacuum drying for 2 h at room temperature, then heated to 80° C. at the temperature rising rate of 10° C./h and dried until the weight was constant, that is, total 119.3 g of finished product was obtained. By determination via Karl Fischer method, the content of water was 1.53%, and the molar yield was 95.4%. It can be seen from FIG. 4 and FIG. 5 that the obtained product is indeed 3-hydroxybenzylamine, and the gas chromatography content reaches more than 99.0%. Various groups of gas chromatography data in FIG. 4 are as follows:

| Number | Retention time (min) | Peak area | Concentration (%) |
|---|---|---|---|
| 1 | 3.862 | 5186747 | 100 |
| Total | | 5186747 | 100 |

Figure 6:
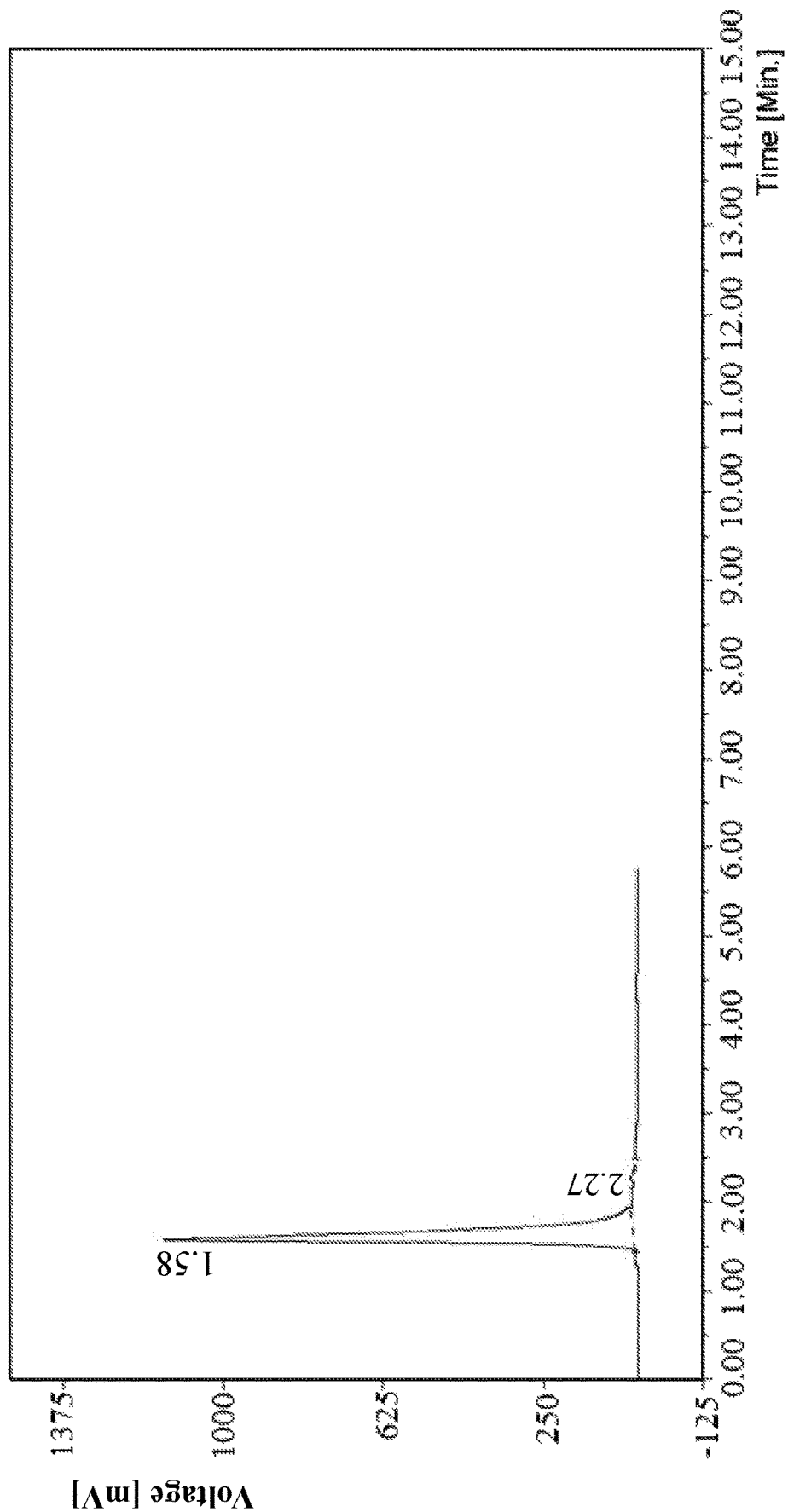
FIG. 6 is a liquid chromatogram of 4-hydroxybenzylamine in Example 3.
Figure 7:
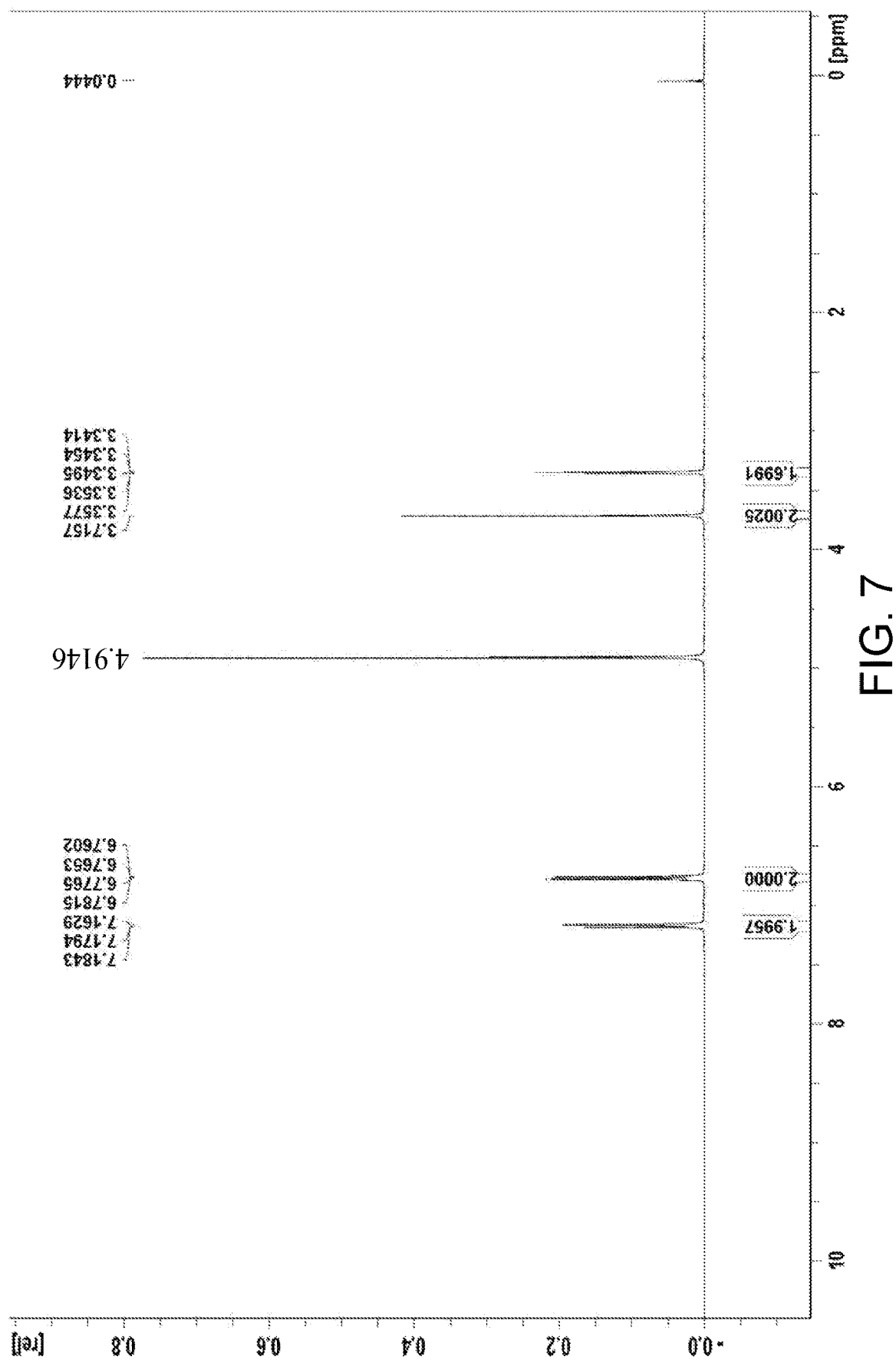
FIG. 7 is a H-NMR Spectrum of 4-hydroxybenzylamine in Example 3.

Example 3: Synthesis of 4-hydroxybenzylamine 970.9 g (3.0 mol) of 25% hydrobromic acid was added into a 1 L reactor equipped with a thermometer, a dropping funnel, an adjustable power heating jacket, a stirrer and a distillation device, and 103.7 g (0.7558 mol) of 4-methoxybenzylamine was added dropwise under the stirring of the stirrer by utilizing the dropping funnel. After the dropwise addition was completed, excess water was removed by heating and distillation until the top temperature of a distillation device reached more than 120° C. (at this moment, the temperature in the reactor reached more than 126° C.), and then the heating rate was reduced so that the distillate flowed back or was distilled out at a very slow rate. The temperature in the reactor was kept to be more than 126° C. The generated gas was absorbed by a solvent or recycled by a refrigeration method to protect the environment until generation of no gas was observed. At this moment, the heating rate was increased again, distillation was continued, and excess hydrobromic acid was recovered until the temperature in the reactor reached more than 132° C., the reactor was slightly cooled, 200 ml of water was added, and a pre-cooled sodium hydroxide aqueous solution with a mass concentration of 40% was dropwise added under the condition of water cooling, so that a precipitate was generated, and then the pre-cooled sodium hydroxide aqueous solution was dropwise added again until the precipitate completely disappeared, the resulting solution was extracted and washed twice with 50 ml*2 of toluene, toluene was recycled from the organic phase, the pH value of the water phase was adjusted to 9-10 with 30.0% hydrochloric acid under the condition of ice water cooling, the water phase was stirred, crystallized and underwent suction filtration, the filter cake was washed with 240 ml of water, then drained and dried in vacuum, namely, a state that the absolute pressure was less than 10 mmHg was formed. The filter cake was subjected to rotary vacuum drying for 2 h at room temperature, then heated to 80° C. at the temperature rising rate of 10° C./h and dried until the weight was constant, that is, total 86.9 g of finished product was obtained. By determination via Karl Fischer method, the content of water was 0.2%, and the molar yield was 92.5%. It can be seen from FIG. 6 and FIG. 7 that the obtained product is indeed 4-hydroxybenzylamine, and the HPLC content reaches more than 99.0%. Various groups of HPLC data in FIG. 6 are as follows:

| Number | Retention time (min) | Peak area | Concentration (%) |
| --- | --- | --- | --- |
| 1 | 1.58 | 8920.50 | 99.24 |
| 2 | 2.27 | 68.53 | 0.76 |
| Total | | 8989.03 | 100 |

Figure 8:
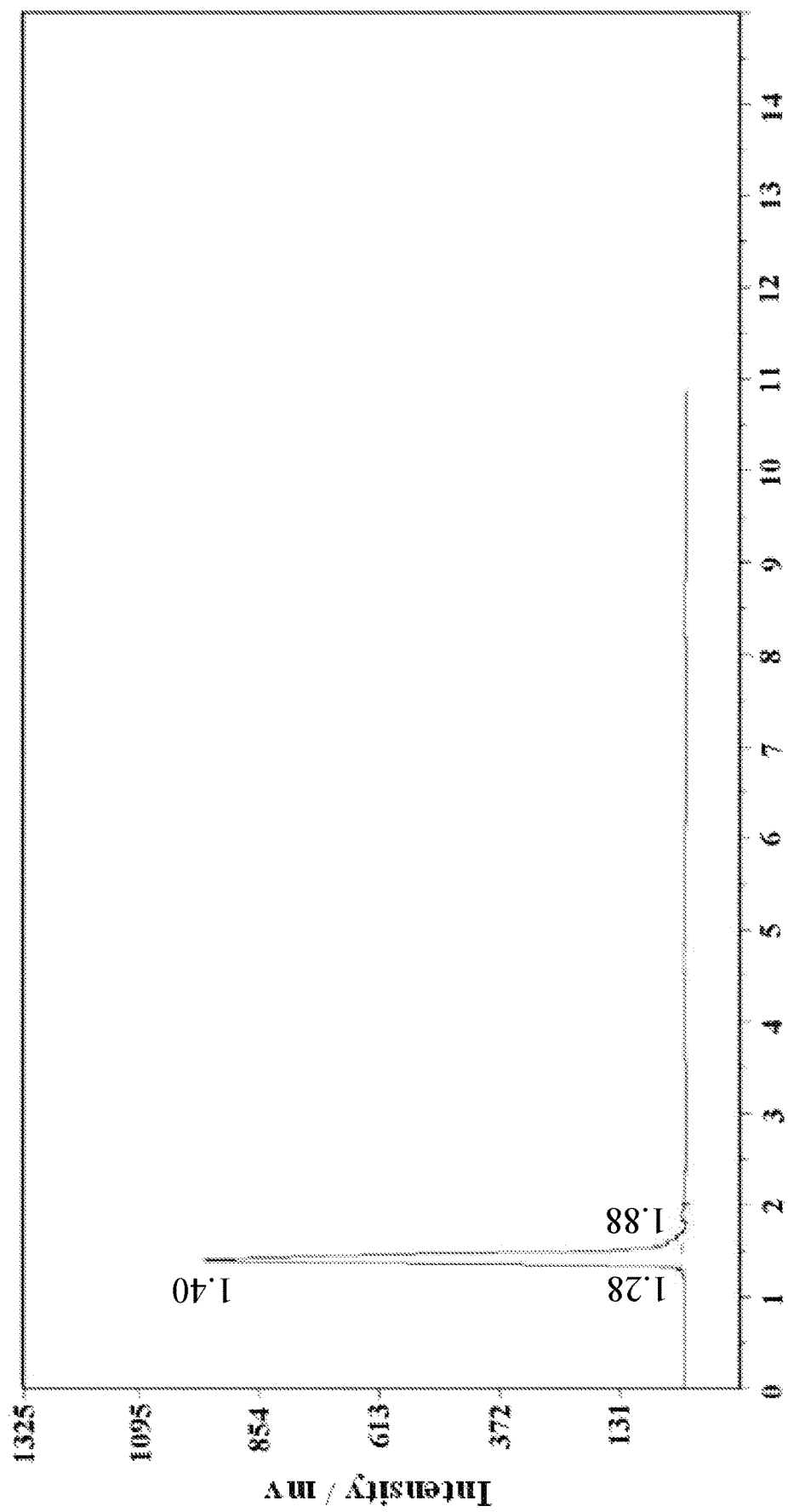
FIG. 8 is a liquid chromatogram of 4-hydroxybenzylamine in Example 4.
Figure 9:
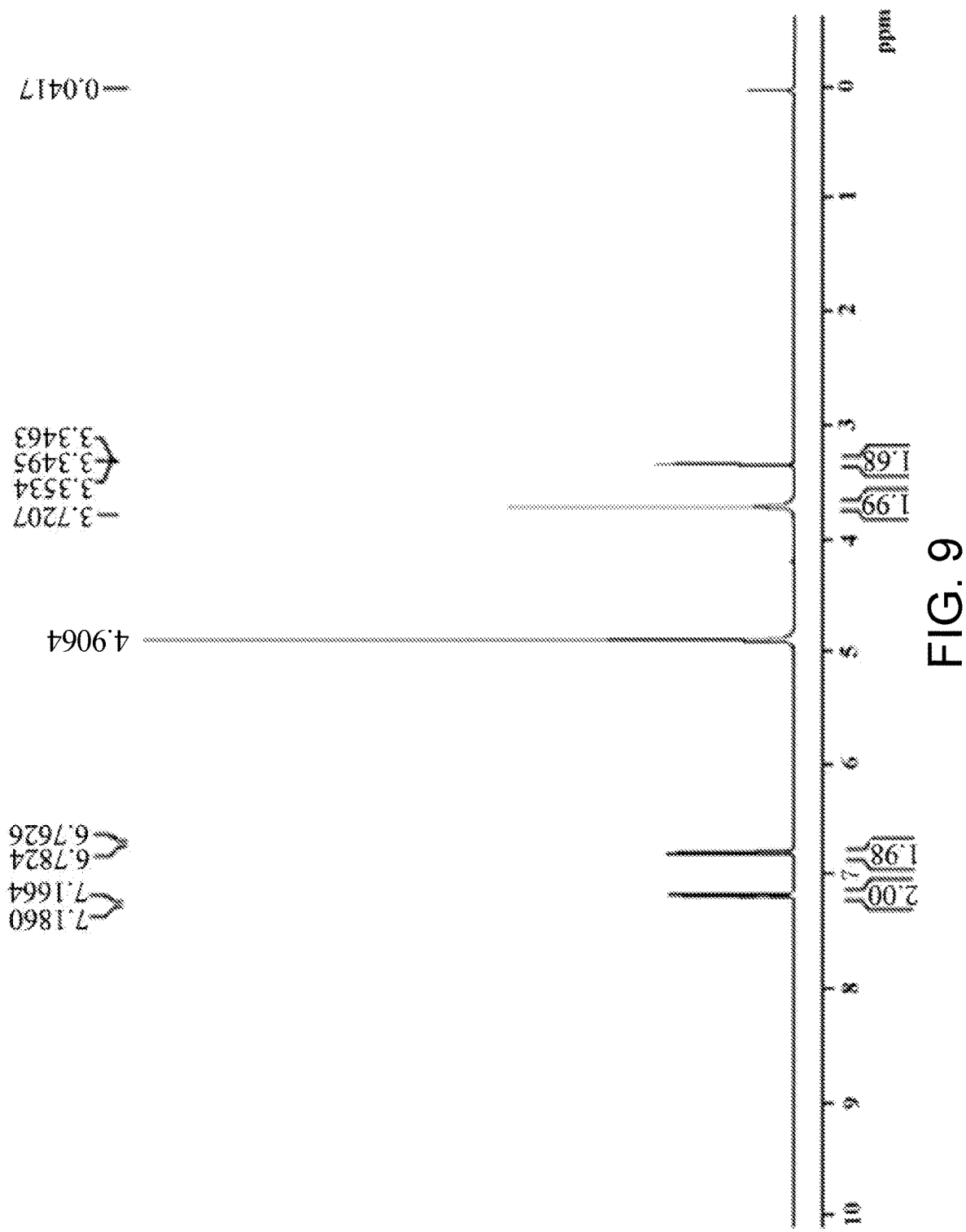
FIG. 9 is a H-NMR Spectrum of 4-hydroxybenzylamine in Example 4.

Example 4: Synthesis of 4-hydroxybenzylamine 231 g (1.27 mol) of 44.5% hydrobromic acid recycled in example 3 was added into a 0.5 L reactor equipped with a thermometer, a dropping funnel, an adjustable power heating jacket, a stirrer and a distillation device, and 43.56 g (0.3175 mol) of 4-methoxybenzylamine was added dropwise under the stirring of the stirrer by utilizing the dropping funnel. After the dropwise addition was completed, excess water was removed by heating and distillation until the top temperature of a distillation device reached more than 120° C. (at this moment, the temperature in the reactor reached more than 126° C.), and then the heating rate was reduced so that the distillate flowed back or was distilled out at a very slow rate. The temperature in the reactor was kept to be more than 126° C. The generated gas was absorbed by a solvent or recycled by a refrigeration method to protect the environment until generation of no gas was observed. At this moment, the heating rate was increased again, distillation was continued, and excess hydrobromic acid was recycled until the temperature in the reactor reached more than 132° C., the reactor was slightly cooled, 60 ml of water was added, and a pre-cooled sodium hydroxide aqueous solution with a mass concentration of 25% was dropwise added under the condition of water cooling, so that a precipitate was generated, and then the pre-cooled sodium hydroxide aqueous solution was dropwise added again until the precipitate completely disappeared, the resulting solution was extracted and washed twice with 30 ml*2 of methyl tertbutyl ether, methyl tertbutyl ether was recycled from the organic phase, the pH value of the water phase was adjusted to 9-10 with 30.0% hydrochloric acid under the condition of ice water cooling, the water phase was stirred, crystallized and underwent suction filtration, a filter cake was washed with 200 ml of water, then drained and dried in vacuum, namely, a state that the absolute pressure was less than 10 mmHg was formed. The filter cake was subjected to rotary vacuum drying for 2 h at room temperature, then heated to 80° C. at the temperature rising rate of 10° C./h and dried until the weight was constant, that is, total 37.7 g of finished product was obtained. By determination via Karl Fischer method, the content of water was 3.56%, and the molar yield was 92.4%. It can be seen from FIG. 8 and FIG. 9 that the obtained product is indeed 4-hydroxybenzylamine, and the HPLC content reaches more than 99.0%. Various groups of HPLC data in FIG. 8 are as follows:

| Number | Retention time (min) | Peak area | Concentration (%) |
| --- | --- | --- | --- |
| 1 | 1.28 | 3.78 | 0.0600 |
| 2 | 1.40 | 6676.74 | 99.40 |
| 3 | 1.88 | 36.56 | 0.5400 |
| Total | | 6717.07 | 100 |

Equipment and instruments involved in the above examples, such as adjustable power heating jackets, stirrers and reactors, are all equipment and instruments commonly used in the prior art.

What is claimed is:
1. A synthesis method of hydroxybenzylamine, comprising the following steps:
step S1: adding hydrobromic acid into a reactor equipped with a thermometer, a dropping funnel, an adjustable power heating jacket, an agitator and a distillation device, dropwise adding methoxybenzylamine under a condition of stirring until the dropwise addition of methoxybenzylamine is ended, heating, and distilling a distillate to remove redundant water;
step S2: when a top temperature of the distillation device reaches more than 120° C., reducing the heating of the adjustable power heating jacket so that the distillate is distilled out at an extremely low rate to keep a temperature in the reactor to be more than 126° C., absorbing a generated gas using an organic solvent, or freezing the generated gas for recycling until generation of no gas is observed;
step S3: continuing to distill the distillate in the step S2, recycling excess hydrobromic acid, and stopping recycling when the temperature in the reactor reaches more than 132° C.;
step S4: slightly cooling the reactor in the step S3, adding water into the reactor, dropwise adding a sodium hydroxide aqueous solution under a condition of cooling so that a precipitate is generated, and continuing to dropwise add the sodium hydroxide aqueous solution until the precipitate completely disappears;
step S5: extracting an organic matter insoluble into alkali in the step S4 with an extraction agent, subsequently recycling the extraction agent from an organic phase, and remaining a water phase; and
step S6: adjusting a pH value of the remaining water phase in the step S5 by adding hydrochloric acid under conditions of ice water cooling, stirring and crystallizing, performing suction filtration, washing, and conducting vacuum drying to obtain the hydroxybenzylamine.
2. The synthesis method of hydroxybenzylamine according to claim 1, wherein a mass concentration of hydrobromic acid in the step S1 is more than 1%.
3. The synthesis method of hydroxybenzylamine according to claim 1, wherein methoxybenzylamine in the step S1 is one of 2-methoxybenzylamine, 3-methoxybenzylamine or 4-methoxybenzylamine.

4. The synthesis method of hydroxybenzylamine according to claim 1, wherein a feeding molar ratio in the step S1 of methoxybenzylamine and hydrobromic acid is 1:2-1:4.

5. The synthesis method of hydroxybenzylamine according to claim 1, wherein a concentration of the sodium hydroxide aqueous solution dropwise added in the step S4 is 1%-60%.

6. The synthesis method of hydroxybenzylamine according to claim 1, wherein the extraction agent for extracting the organic matter insoluble into alkali in the step S5 is an ether substance or a homologue of benzene, the ether substance is ether, propyl ether, isopropyl ether, butyl ether or methyl tert-butyl ether; the homologue of benzene is benzene, toluene or xylene.

7. The synthesis method of hydroxybenzylamine according to claim 1, wherein a concentration of hydrochloric acid in the step S6 is 1%-37.5%.

8. The synthesis method of hydroxybenzylamine according to claim 1, wherein the pH value in the step S6 is adjusted to 9-10.

9. The synthesis method of hydroxybenzylamine according to claim 1, wherein conditions of vacuum drying in the step S6 are as follows: an absolute pressure is less than 10 mmHg for 2 h at a drying temperature of room temperature, and then the drying temperature is raised to 80° C. at a temperature rising rate of 10° C./h until a weight of the the hydroxybenzylamine is constant.

10. The synthesis method of hydroxybenzylamine according to claim 1, wherein a mass concentration of hydrobromic acid in the step S1 is 10%-48%.

11. The synthesis method of hydroxybenzylamine according to claim 1, wherein a feeding molar ratio in the step S1 of methoxybenzylamine and hydrobromic acid is 1:2.5-1:4.

12. The synthesis method of hydroxybenzylamine according to claim 1, wherein a concentration of the sodium hydroxide aqueous solution dropwise added in the step S4 is 10%-50%.

13. The synthesis method of hydroxybenzylamine according to claim 1, wherein a concentration of hydrochloric acid in the step S6 is 10%-37.5%.

\* \* \* \* \*